United States Patent
Kim et al.

(10) Patent No.: US 12,023,515 B2
(45) Date of Patent: Jul. 2, 2024

(54) LASER TREATMENT OF SKIN LESIONS UNDER DERMAL VASOCONSTRICTION

(71) Applicants: Ilooda, Co., Ltd., Gyeonggi-do (KR); Sungil In, Suwon-si (KR); Youngjin Kim, Seoul (KR)

(72) Inventors: Yonghan Kim, Gyeonggi-do (KR); Sungil In, Suwon-si (KR); Youngjin Kim, Seoul (KR)

( * ) Notice: Subject to any disclaimer, the term of this patent is extended or adjusted under 35 U.S.C. 154(b) by 230 days.

(21) Appl. No.: 17/339,314

(22) Filed: Jun. 4, 2021

(65) Prior Publication Data
US 2021/0402209 A1 Dec. 30, 2021

Related U.S. Application Data

(60) Provisional application No. 63/035,569, filed on Jun. 5, 2020.

(51) Int. Cl.
| | |
|---|---|
| *A61N 5/06* | (2006.01) |
| *A61B 17/00* | (2006.01) |
| *A61B 18/00* | (2006.01) |
| *A61B 18/20* | (2006.01) |
| *A61N 5/067* | (2006.01) |

(52) U.S. Cl.
CPC ........... *A61N 5/0616* (2013.01); *A61N 5/067* (2021.08)

(58) Field of Classification Search
CPC ...... A61N 5/06–2005/073; A61B 18/20–18/28
USPC ..................... 606/2–19; 607/88–94
See application file for complete search history.

(56) References Cited

U.S. PATENT DOCUMENTS

| | | |
|---|---|---|
| 6,096,029 A | 8/2000 | O'Donnel, Jr. |
| 6,273,885 B1 | 8/2001 | Koop et al. |
| | (Continued) | |

FOREIGN PATENT DOCUMENTS

| | | |
|---|---|---|
| WO | WO 2013/075006 A1 | 5/2013 |
| WO | WO 2013/075016 A1 | 5/2013 |
| | (Continued) | |

OTHER PUBLICATIONS

Zenzie et al., Evaluation of Cooling Methods for Laser Dermatology, (2000), Lasers in Surgery and Medicine 26:130-144 (Year: 2000).*

(Continued)

*Primary Examiner* — Jonathan T Kuo
*Assistant Examiner* — Vynn V Huh
(74) *Attorney, Agent, or Firm* — Covington & Burling LLP; Einar Stole; W. Kiersten Choi

(57) ABSTRACT

A method for treating a skin lesion can include lowering a temperature of a treatment site to a temperature range sufficient to induce vasoconstriction in a dermis of the treatment site and administering a laser light through a medium to the skin lesion while maintaining the temperature of the treatment site within the temperature range. The medium can include a first portion and a second portion, where the laser light is transmitted through the first portion and the second portion sequentially, the second portion includes a contact surface for contacting the treatment site, and the second portion has a higher thermal conductivity than the first portion. The method can further include identifying the skin lesion and analyzing one or more characteristics of the skin lesion.

26 Claims, 17 Drawing Sheets

(56) References Cited

U.S. PATENT DOCUMENTS

| | | | |
|---|---|---|---|
| 2007/0010861 A1* | 1/2007 | Anderson | A61F 7/00 607/96 |
| 2007/0093798 A1* | 4/2007 | DeBenedictis | A61B 18/203 606/9 |
| 2008/0082149 A1 | 4/2008 | Bernstein | |
| 2018/0214300 A1 | 8/2018 | Anderson et al. | |
| 2019/0374287 A1 | 12/2019 | Anderson et al. | |
| 2021/0077823 A1* | 3/2021 | Schomacker | A61F 7/007 |

FOREIGN PATENT DOCUMENTS

| | | |
|---|---|---|
| WO | WO 2015/021462 A1 | 2/2015 |
| WO | WO 2015/123420 A1 | 8/2015 |

OTHER PUBLICATIONS

Alba et al., "Cold-induced cutaneous vasoconstriction in humans: Function, dysfunction and the distinctly counterproductive", Experimental Physiology, 104, 1202-1214, (2019).

G. B. Altshuler et al., "Contact cooling of the skin", Phys. Med. Biol. 44, 1003-1023, (Jan. 1999).

Anupam Das et al., "Cooling Devices in Laser therapy", J Cutan Aesthet Surg., 9(4), 215-219, (Oct-Dec. 2016).

En Hyung Kim et al., "The vascular characteristics of melasma", Journal of Dermatological Science, 46, 111-116, (2007).

Taro Kono, MD et al., "Q-Switched Ruby Versus Long-Pulsed Dye Laser Delivered With Compression for Treatment of Facial Lentigines in Asians", Lasers in Surgery and Medicine, 38:94-97, (2006).

Q. Geng et al., "Temperature Limit Values for Touching Cold Surfaces with the Fingertip", Ann. Occup. Hyg., vol. 50, No. 8, 851-862, (2006).

K. M. Kelly and J. Stuart Nelson, "Overview of lasers in dermatology," Proc. SPIE, vol. 10297 (vol. CR75), (Jan. 24, 2000).

J. Stuart Nelson, MD et al., "Active Skin Cooling in Conjunction with Laser Dermatologic Surgery", Seminars in Cutaneous Medicine and Surgery, vol. 19, No. 4, 253-266, (Dec. 2000).

Henry H. L. Chan, FRCP et al., "Role of Skin Cooling in Improving Patient Tolerability of Q-Switched Alexandrite (QS Alex) Laser in Nevus of Ota Treatment", Lasers in Surgery and Medicine, 32:148-151, (2003).

Shiseido Group, "Shiseido Succeeds in In Vivo Visualization of Dermal Capillaries—Discovery of Malformation of Vascular Plexuses in Hyperpigmented Skin-", Shiseido Company, Limited, (Sep. 2017).

Kayvan Shokrollahi et al., "Lasers: Principles and Surgical Application", The Journal of Surgery, vol. 2, Issue 1, 28-34, (2004).

H.H. Zenzie, MS et al., "Evaluation of Cooling Methods for Laser Dermatology", Lasers in Surgery and Medicine, 26, 130-144, (2000).

* cited by examiner

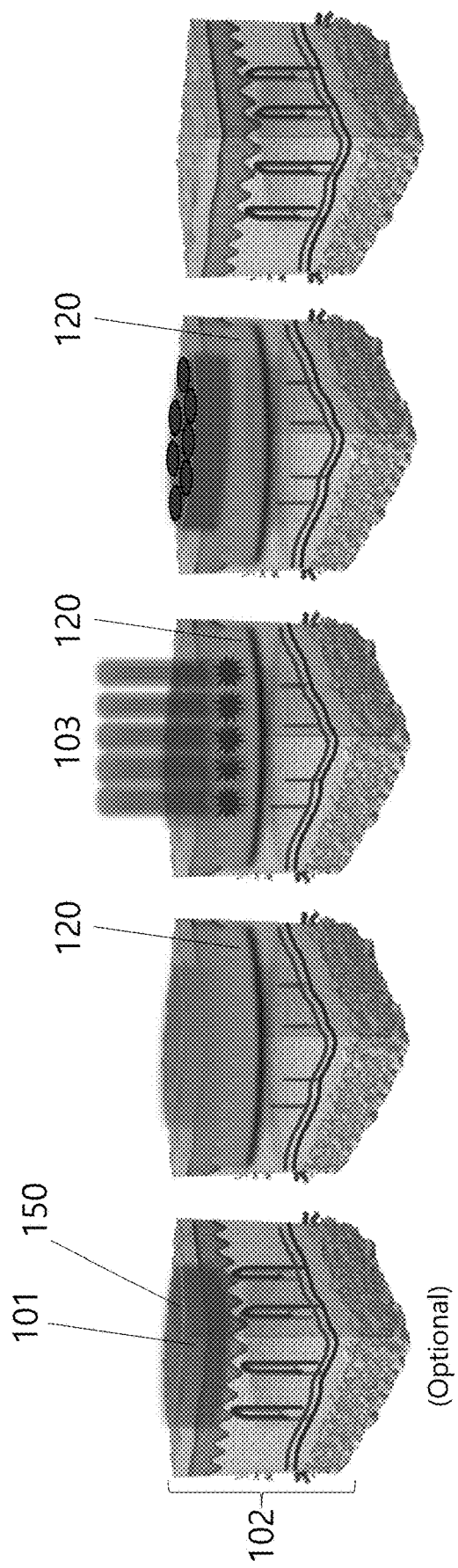

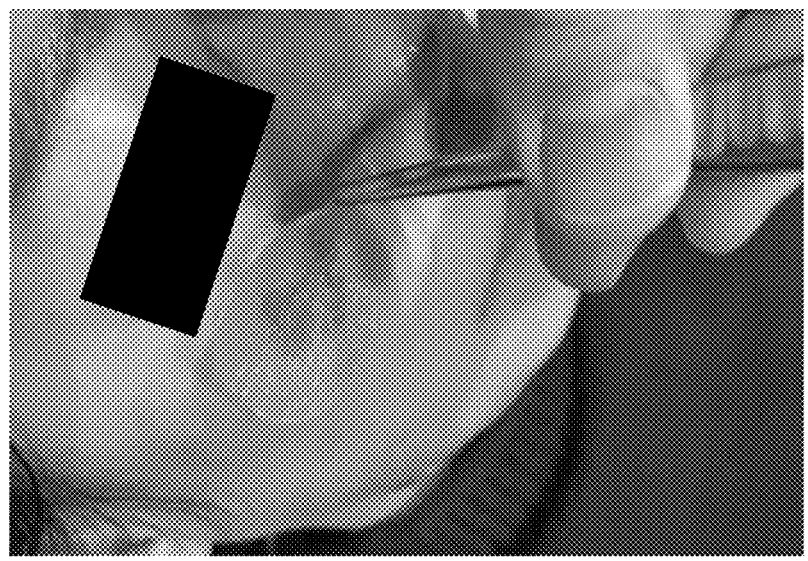
FIG. 11B
FIG. 11A

LASER TREATMENT OF SKIN LESIONS UNDER DERMAL VASOCONSTRICTION

CLAIM OF PRIORITY

This application claims priority to U.S. Provisional Patent Application No. 63/035,569 filed on Jun. 5, 2020, which is hereby incorporated by reference in its entirety.

TECHNICAL FIELD

This invention relates to dermatological laser treatment.

BACKGROUND

Melanin is biosynthesized in melanocytes located in the basement membrane of skin. Melanin is transported in the form of melanosomes to the surrounding keratinocytes along via the dendrites of melanocytes. When melanin is excessively produced or existing melanin is more actively transferred to keratinocytes by a certain stimulation, various pigmented lesions can be formed or pre-existing hyperpigmentation can be exacerbated. Excessive melanin production can be caused by ultraviolet (UV) exposure or inflammatory skin reactions.

Laser treatment has been widely used in dermatology to treat various vascular and pigmented skin lesions, tattoos, benign skin tumors, precancerous lesions, non-melanoma skin cancers in situ, and minimally invasive skin cancers. Conventional laser treatment methods for skin lesions are generally safe and effective but can cause side effects, such as burn, wound infection, hypersensitivity reaction to topical anesthesia, as well as chronic or permanent side effects, such as persistent post-laser erythema (PLE), post-inflammatory hyperpigmentation (PIH) and scarring.

SUMMARY

Generally, a method for treating a skin lesion can include lowering a temperature of a treatment site to a temperature range sufficient to induce vasoconstriction in a dermis of the treatment site and administering a laser light through a medium to the skin lesion while maintaining the temperature of the treatment site within the temperature range.

In certain embodiments, the medium can include a first portion and a second portion, where the laser light is transmitted through the first portion and the second portion sequentially, the second portion includes a contact surface for contacting the treatment site and the second portion has a higher thermal conductivity than the first portion.

In certain embodiments, the first portion and the second portion can be optically transparent.

In certain embodiments, the first portion can include quarts, sapphire, crystal, poly(methyl methacrylate), or polystyrene.

In certain embodiments, the second portion can include quarts, sapphire, crystal, poly(methyl methacrylate), or polystyrene.

In certain embodiments, a beam splitter can be located between the first portion and the second portion.

In certain embodiments, the first portion and the second portion can be separated by sealed air.

In certain embodiments, the lowering the temperature of the treatment site can include contacting the treatment site with the contact surface of the second portion of the medium.

In certain embodiments, the contacting the treatment site with the contact surface of the second portion of the medium can include compressing the surface of the treatment site with the contact surface of the second portion of the medium.

In certain embodiments, the lowering the temperature of the treatment site can include administering a drug to induce vasoconstriction of the treatment site before administering the laser light.

In certain embodiments, the laser light can have a wavelength between about 300 nm and about 2500 nm.

In certain embodiments, the laser light is a pulsed light.

In certain embodiments, the laser light has a fluence of 0-3000 $J/cm^2$.

In certain embodiments, the method can further include applying an antifreeze on a surface of the treatment site or on the contact surface of the second portion of the medium.

In certain embodiments, the temperature range of the treatment site sufficient to induce vasoconstriction in a dermis of the treatment site can be between 0° C. and 20° C.

In certain embodiments, the medium can have a temperature between −30° C. and 0° C.

In certain embodiments, the method can further include identifying the skin lesion and analyzing one or more characteristics of the skin lesion.

In certain embodiments, the one or more characteristics can be location, boundary, size, thickness, or pigment level of the skin lesion.

In certain embodiments, the skin lesion is a pigmented lesion.

In certain embodiments, the skin lesion is a non-pigmented lesion.

Generally, a device for treating a skin lesion can include a source for generating a laser light, a medium for transmitting the laser light, where the medium includes a first portion and a second portion, the laser light is transmitted through the first portion and the second portion sequentially, the second portion includes a contact surface for contacting the treatment site, and the second portion has a higher thermal conductivity than the first portion.

In certain embodiments, the laser light can have a wavelength between about 300 nm and about 2500 nm.

In certain embodiments, the laser light can be a pulsed light.

In certain embodiments, the laser light can have a fluence of 0-3000 $J/cm^2$.

In certain embodiments, the first portion and the second portion can be optically transparent.

In certain embodiments, the first portion can include quarts, sapphire, crystal, poly(methyl methacrylate), or polystyrene.

In certain embodiments, the second portion can include quarts, sapphire, crystal, poly(methyl methacrylate), or polystyrene.

In certain embodiments, the device can further include a beam splitter located between the first portion and the second portion.

In certain embodiments, the first portion and the second portion can be separated by sealed air.

In certain embodiments, the device can further include a cooling unit to lower a temperature of the medium to a target temperature range.

In certain embodiments, the target temperature range of the medium can be from −30° C. to 0° C.

In certain embodiments, the cooling unit can include a thermo-electric cooler, cooling air, cooling gas, or cooling liquid.

In certain embodiments, further comprising a metal unit that can be placed between the cooling unit and the medium.

In certain embodiments, the metal unit can include a temperature sensor.

In certain embodiments, the temperature sensor can detect the temperature of the medium.

In certain embodiments, the temperature sensor can detect a temperature of the cooling unit.

In certain embodiments, the temperature sensor can detect a temperature of the treatment site.

In certain embodiments, the skin lesion is a pigmented lesion.

In certain embodiments, the skin lesion is a non-pigmented lesion.

Generally, a system for treating a skin lesion can include a source for generating a laser light, a medium for transmitting the laser light, where the medium includes a first portion and a second portion, the laser light is transmitted through the first portion and the second portion sequentially, the second portion includes a contact surface for contacting the treatment site, and the second portion has a higher thermal conductivity than the first portion, a cooling unit to lower a temperature of the medium to a target temperature range, a beam splitter located between the first portion and the second portion, where the beam splitter sends an image of the skin lesion to an image-capturing device, and a controller operatively coupled to the image-capturing device to analyze one or more characteristics of the skin lesion, where the controller guides the laser light to treat the skin lesion according to the one or more characteristics.

In certain embodiments, the laser light can have a wavelength between about 300 nm and about 2500 nm.

In certain embodiments, the laser light can be a pulsed light.

In certain embodiments, the laser light can have a fluence of 0-3000 J/cm$^2$.

In certain embodiments, the first portion and the second portion can be optically transparent.

In certain embodiments, the first portion and the second portion can be separated by sealed air.

In certain embodiments, the first portion can include quarts, sapphire, crystal, poly(methyl methacrylate), or polystyrene.

In certain embodiments, the second portion can include quarts, sapphire, crystal, poly(methyl methacrylate), or polystyrene.

In certain embodiments, the target temperature range of the medium can be from −30° C. to 0° C.

In certain embodiments, the cooling unit can include a thermo-electric cooler, cooling air, cooling gas, or cooling liquid.

In certain embodiments, the image can be a real-time image.

In certain embodiments, the one or more characteristics can be location, boundary, size, thickness, or pigment level of the skin lesion.

In certain embodiments, the skin lesion is a pigmented lesion.

In certain embodiments, the skin lesion is a non-pigmented lesion.

Generally, a system for treating a skin lesion can include a source for generating a laser light, a medium for transmitting the laser light, wherein the medium includes a first portion and a second portion, where the laser light is transmitted through the first portion and the second portion sequentially, the second portion includes a contact surface for contacting a treatment site, and the second portion has a higher thermal conductivity than the first portion, and a cooling unit to lower a temperature of the medium to a target temperature range.

In certain embodiments, the laser light can have a wavelength between about 300 nm and about 2500 nm.

In certain embodiments, the laser light can be a pulsed light.

In certain embodiments, the laser light can have a fluence of 0-3000 J/cm$^2$.

In certain embodiments, the first portion and the second portion can be optically transparent.

In certain embodiments, the first portion and the second portion can be separated by sealed air.

In certain embodiments, the first portion can include quarts, sapphire, crystal, poly(methyl methacrylate), or polystyrene.

In certain embodiments, the second portion can include quarts, sapphire, crystal, poly(methyl methacrylate), or polystyrene.

In certain embodiments, the target temperature range of the medium can be from −30° C. to 0° C.

In certain embodiments, the cooling unit can include a thermo-electric cooler, cooling air, cooling gas, or cooling liquid.

In certain embodiments, the system can further include a metal unit that is placed between the cooling unit and the medium.

In certain embodiments, the metal unit can include a temperature sensor.

In certain embodiments, the temperature sensor can detect the temperature of the medium.

In certain embodiments, the controller can be operatively coupled to the temperature sensor to control the temperature of the medium.

In certain embodiments, the temperature sensor can detect a temperature of the cooling unit.

In certain embodiments, the controller can be operatively coupled to the temperature sensor to control the temperature of the cooling unit.

In certain embodiments, the temperature sensor can detect a temperature of the treatment site.

In certain embodiments, the controller can be operatively coupled to the temperature sensor to control the temperature of the treatment unit.

In certain embodiments, the skin lesion is a pigmented lesion.

In certain embodiments, the skin lesion is a non-pigmented lesion.

Other aspects, embodiments, and features will be apparent from the following description, the drawings, and the claims.

BRIEF DESCRIPTION OF THE DRAWINGS

FIG. 2A shows that treatment site can be pre-treated with a local anesthetic and epinephrine to promote further vasoconstriction. FIG. 2B shows a step of lowering the temperature of treatment site to a target temperature range sufficient to induce vasoconstriction in a dermis of treatment site. FIG. 2C shows a step of administering laser light 103 to the skin lesion while maintaining the temperature of treatment site 120 within the target temperature range. FIG. 2D shows that this method can minimize the damages on the dermal vasculature while treating the skin lesion. FIG. 2E shows that side effects, such as PLE, PIH, and scars, can be significantly reduced.

FIG. 11A is a photo showing removal of epidermis including the skin lesion after the laser treatment according to the instant method. FIG. 11B is an illustration showing the laser shots and the chromophores residing on the basement membrane.

DETAILED DESCRIPTION

Figure 1B:
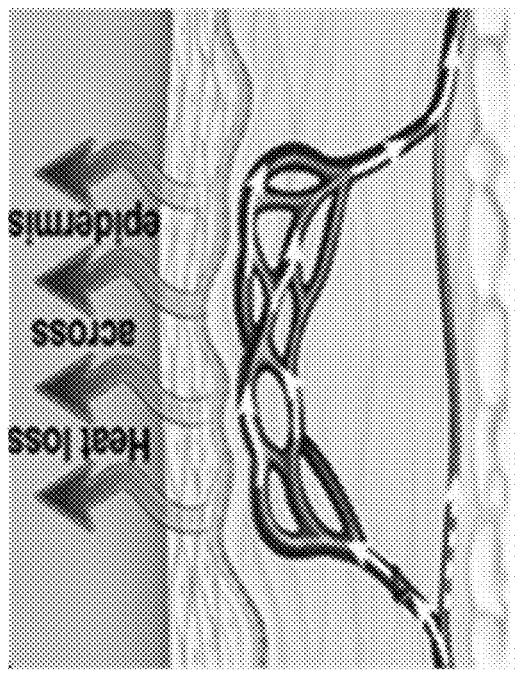
FIG. 1B is a schematic of blood flow under dermal vasoconstriction.

As used herein, the term "include" means include but not limited to.

As used herein, the term "pigmented lesion" includes any lesion that includes any kind of pigment. The pigment can be natural (e.g. melanin or oxyhemoglobin) or artificial (e.g. tattoo pigments).

Various lasers can be used to treat pigmented lesions in the skin by taking advantage of the absorption of specific wavelengths of light by the pigmented lesion. In other words, the pigmented lesion is a chromophore for that specific wavelength of the laser light. Typically, lasers with a pulse width shorter than the thermal relaxation time (TRT) of the chromophore can be used to treat a pigmented lesion because a shorter TRT can minimize the damage to the surrounding skin tissue by selectively destroying the target pigment with high-power energy, while minimizing the duration of the absorption of photoelectrons by the chromophore and thereby minimizing the conversion to thermal energy and diffusion to nearby skin tissues and cells. However, the high-power energy administered by laser inevitably leads to inflammatory reaction and tissue damage followed by the wound healing process. In fact, many laser skin treatment modalities take advantage of the wound healing process to promote skin regeneration. However, when an excessive reaction is incurred by the laser treatment, there can be undesirable side effects, PLE, PIH, and scars.

Laser treatment can also be used to non-pigmented skin lesions. Except for melanin, most of the chromophores in the skin, such as water, oxyhemoglobin, and sebaceous glands, mostly reside in dermis. Currently, when laser treatments target lesions in dermis, the fluence and energy level should be low enough to prevent possible burn in the epidermis and damages in the surrounding dermal tissues and vasculature. Although there are existing cooling devices used for lasers, they are mostly designed to prevent the burn in the epidermis and cannot sufficiently cool the dermis to allow effective and efficient treatments with sufficient energy while preventing tissue damages and various side effects. Under these limitations, the energy level delivered by the existing lasers is not sufficient to target lesions in dermis, such as collagen, hair, and sebaceous glands, often requiring multiple and prolonged laser treatment sessions.

When the tissue damages occur after a laser treatment, inflammatory cells migrate to the damaged sites via capillaries in dermis, interact with cells surrounding the damaged sites, and secrete various cytokines that trigger inflammatory reactions. These cytokines also trigger the wound healing process in the damaged skin to generate new skin tissues. When the cytokines lead to excessive inflammatory reactions, they can promote formation of new blood vessels and hyper-proliferation of extracellular matrix and stimulate melanocytes to produce an excessive amount of melanin in the damaged site. As a result, common side effects, such as PLE, scars, and PIH, can be resulted from the laser treatment. In some cases, these are temporary phenomena that can disappear as the wound is healed. However, in case of severe tissue damages, side effects can be quite serious and last for a long time, resulting in prolonged erythema and undesirable hyperpigmentation.

Lasers most commonly used for skin lesions use the wavelengths of light that are highly absorbed by oxyhemoglobin in the vasculature as well as the target chromophores. The absorption of the high-power energy by oxyhemoglobin can lead to bleeding of the capillaries (petechiae) followed by dermal edema and purpura. As the fluence of the laser light increases, capillary damages also increase. Currently, topical anesthetic creams, prescription drugs before and after the laser treatment, and/or wet dressings are used to minimize the pain or side effects caused by laser treatment, but they have very limited effects. Until now, the side effects, such as PLE, PIH, and scars, have been considered inevitable with the conventional laser treatment modalities, and post-treatment management has been emphasized more than prevention of the side effects.

Dermis is the most seriously impacted by the high-power energy from laser light because of its vasculature containing oxyhemoglobin in the red blood cells, which are the chromophores for many types of conventional lasers in dermatology. Dermal capillaries can be damaged by absorption of the high-power energy, and the inflammatory cells migrating through the capillaries can produce cytokines that would trigger the inflammatory reaction. Once started, the inflammatory reaction can induce even larger scale of inflammatory cell migration to the damaged site to exacerbate the ongoing reaction. Consequently, amplification and persistent inflammatory reactions by the migrated inflammatory cells can delay the skin regeneration at the damaged site, which is most often associated with a serious level of PLE, PIH, and scars.

Figure 1A:
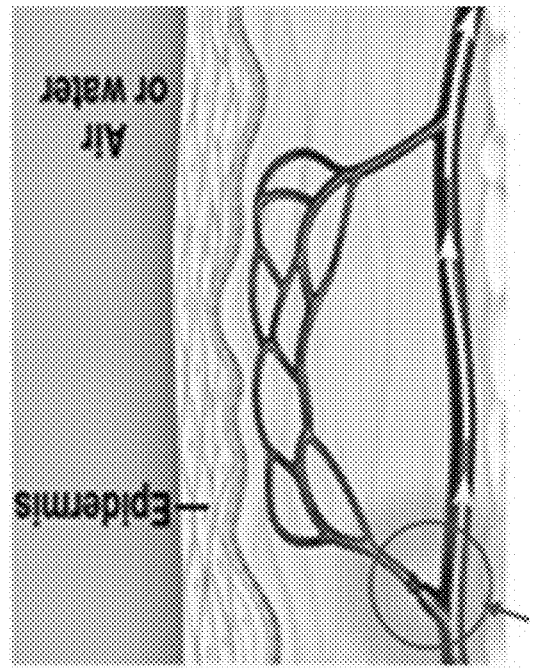
FIG. 1A is a schematic of blood flow in the normal capillary loop in dermis.

To overcome the shortcomings of the conventional laser treatment, dermal vasoconstriction can be induced to trigger a short reflex action of the autonomic nervous system to maintain the body temperature. FIG. 1A is a schematic of blood flow in the normal capillary loop in dermis. FIG. 1B is a schematic of blood flow under dermal vasoconstriction. The reflex action followed by the dermal vasoconstriction can temporarily contract precapillary sphincter and shunt the blood flow only to the vascular plexus before the sphincter (FIG. 1B). By doing so, blood flows to major dermal capillaries can be briefly shut down. When the amount of red blood cells is decreased in dermal capillaries, untargeted chromophores (e.g. oxyhemoglobin) that would respond to the laser light would decrease. As a result, damages to the capillaries can be reduced, thereby reducing the amount of inflammatory cells that would migrate to the damaged site. Consequently, overall inflammatory responses and side effects to the laser light can be significantly reduced, which would promote faster wound healing and skin regeneration. This method thus named as Vasculature Salvage Laser Surgery ("VSLS").

Dermal vasoconstriction can be achieved by lowering the skin temperature to a target range using a cooling device operatively coupled to the laser. However, none of the existing cooling methods are adequate to sufficiently induce dermal vasoconstriction to prevent side effects associated with the laser treatment. Currently, there are two types of cooling methods for lasers: contact-type cooling and non-contact cooling. In case of the contact cooling, the skin would be in contact with a solid medium with a temperature of 0° C. or higher. Cooling gas can lower the temperature to 0° C. or lower, but it only operates for a very short period of time, about 10 to 100 milliseconds. Neither of these methods are sufficient to induce dermal vasoconstriction. Further, the dynamic cooling device, mostly used for long-pulsed lasers whose main purposes are hair removal, vascular lesions, and dermal heating to induce skin tightening, uses a cooling burst of cryogen for milliseconds before a laser shot, and when there is a mismatch between the cooling burst and the laser shot, blisters and scars can be formed. Contact cooling has been used for Intense Pulsed Light (IPL) where the pulse duration is millisecond range, but IPL is a spectral light, different from a single wavelength of light like laser. As for the Q-switched lasers, no separate cooling device has been used due to the nanosecond range of very short pulse duration and the relatively low energy level. However, the lack of separate cooling limits the fluence and energy level of the laser application, which results in ineffective and inefficient treatments, serious side effects, and unsatisfactory outcomes.

When the laser light is administered under dermal vasoconstriction, much higher energy can be applied at a time compared to the conventional method. For example, in case of Q-switched 532 nm lasers with a 3 mm beam spot size, a fluence range of 0.6-1.0 J/cm$^2$ has been typically recommended by laser manufacturers, and a fluence range of 0.6-0.8 J/cm$^2$ has been most commonly used by clinicians. With the conventional laser treatment methods, a higher fluence would results in major capillary ruptures because the absorption by the oxyhemoglobin would be too strong. This would be accompanied by serious side effects, such as pain, edema, petechiae, ecchymoses, and severe PIH. However, when the treated site is cooled to a temperature sufficient to induce dermal vasoconstriction, up to 20 times of energy can be applied at a time without any significant side effects.

FIGS. 2A-2E show schematics of laser treatment for a skin lesion under dermal vasoconstriction. In certain embodiments, the skin lesion can be a pigmented skin lesion. In certain other embodiments, the skin lesion can be a non-pigmented skin lesion. This method enables treating skin lesion 101 in skin 102 using laser light 103 while minimizing undesirable side effects caused by the laser. The method can preserve the dermal vasculature in a treatment site 120 as much as possible while obtaining a desired therapeutic effect. Treatment site 120 includes a skin surface that contacts the medium of the laser light and a volume of the skin underneath that skin surface that laser light 103 affects. Temporarily reducing the amount of red blood cells in the capillaries in treatment site 120 during the laser treatment can reduce the amount of unwanted chromophores that would respond to laser light 103 and thereby minimize the effect of the laser energy on the capillaries. This can be accomplished by lowering the temperature of treatment site 120 to a target temperature range sufficient to induce vasoconstriction in a dermis of treatment site 120 (FIG. 2B) and administering laser light 103 to the skin lesion while maintaining the temperature of treatment site 120 within the target temperature range (FIG. 2C). In certain embodiments, treatment site 120 can be pre-treated with a local anesthetic and epinephrine 150 to promote further vasoconstriction (FIG. 2A). In certain other embodiments, treatment site 120 can be compressed to minimize the blood flow. This method can minimize the damages on the dermal vasculature while treating the skin lesion (FIG. 2D), and side effects, such as PLE, PIH, and scars, can be significantly reduced (FIG. 2E). In certain embodiments, the method can further include identifying the skin lesion and analyzing one or more characteristics of the skin lesion. In certain embodiments, the one or more characteristics are location, boundary, size, thickness, or pigment level of the skin lesion.

Figure 3:
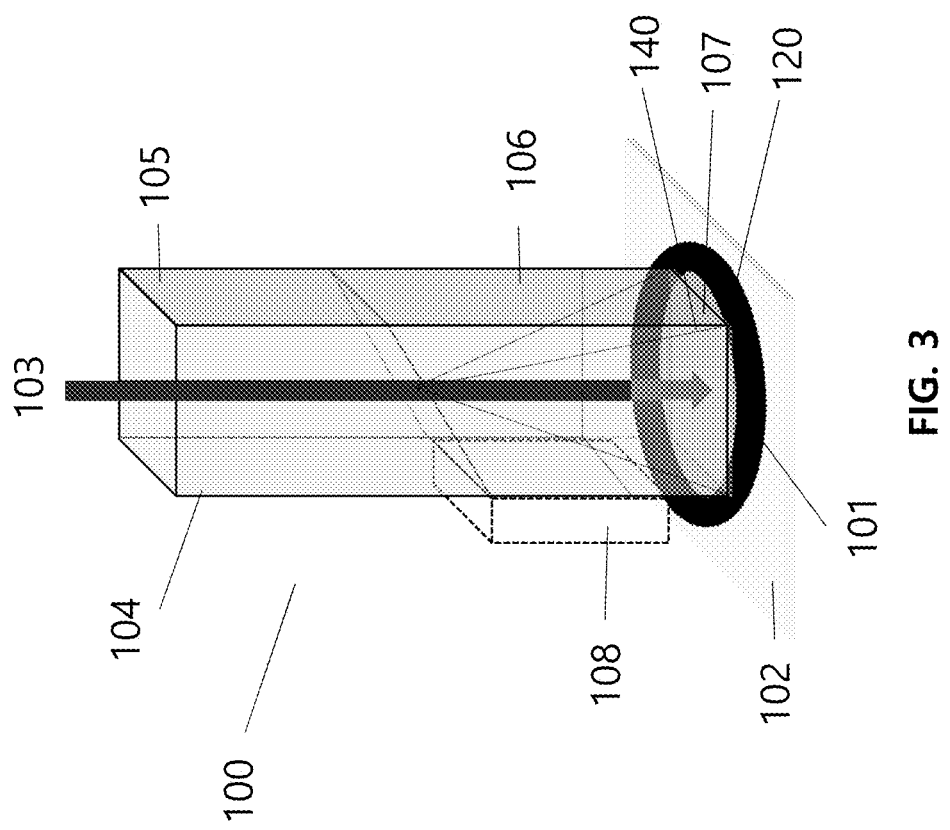
FIGS. 3-6 are embodiments of a device for treating a skin lesion under dermal vasoconstriction.

As depicted in FIG. 3, a device 100 for treating skin lesion 101 in skin 102 using laser light 103 while minimizing undesirable side effects of the laser can include a source (not shown) for generating laser light 103, a medium 104 for transmitting laser light 103, where medium 104 includes a first portion 105 and a second portion 106. Laser light 103 can be transmitted through first portion 105 and second portion 106 sequentially. Second portion 106 can include a contact surface 107 for contacting the surface of treatment site 120. In certain embodiments, second portion 106 can have a higher thermal conductivity than first portion 105. In certain embodiments, device 100 can include a cooling unit 108 to lower the temperature of medium 104 to the target temperature range. Cooling unit 108 can include a thermoelectric cooler, cooling air, cooling gas, or cooling liquid. In certain embodiments, the cooling liquid can be cooling water.

Figure 4:
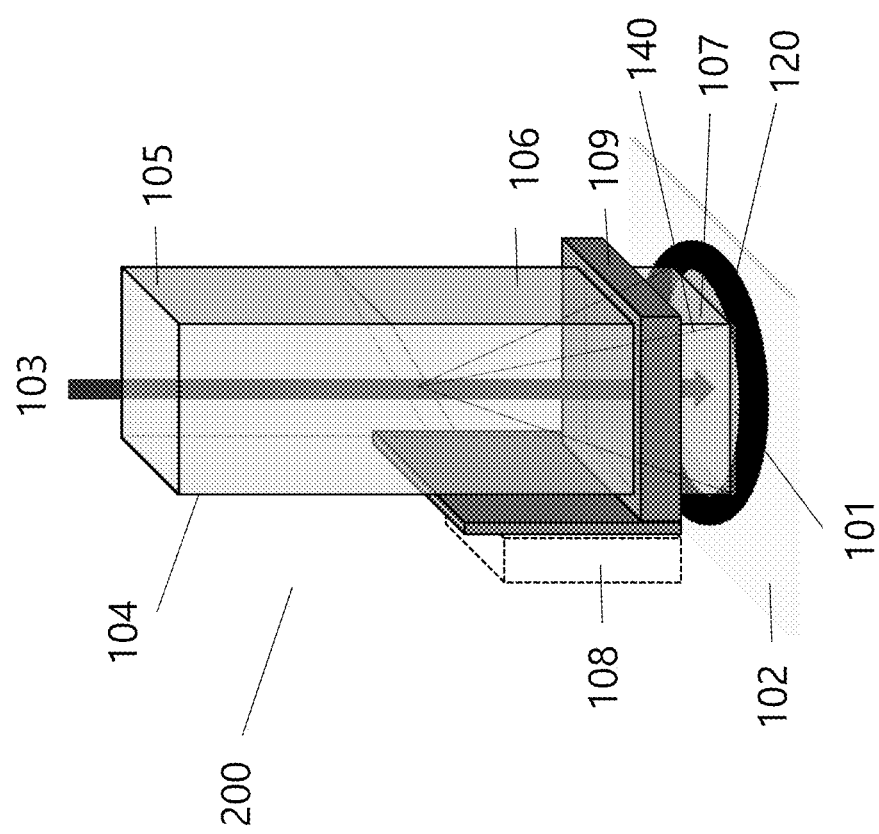

As depicted in FIG. 4, device 200 can further include a metal unit 109 placed between medium 104 and cooling unit 108. Metal unit 109 can be cooled by cooling unit 108 and in turn cool medium 104. Metal unit 109 can further include a temperature sensor (not shown). The temperature sensor can detect a temperature of cooling unit 108, a temperature of medium 104, and/or a temperature of treatment site 120.

In certain embodiments, laser light 103 can be pulsed light. Laser light can be either long-pulsed light or short-pulsed light. Typical pulse duration of the long-pulsed light or the short-pulse light should be well-known to those skilled in the art. In certain embodiments, laser light 103 can have a wavelength between about 300 nm and about 2500 nm. In certain embodiments, the source of laser light 103 can be a Q-switched laser. For example, a Q-switched 694 nm ruby, a Q-switched 755 nm alexandrite, or a Q-switched 532 nm/1064 nm Nd:YAG laser can be used. In certain other embodiments, the source of laser light 103 can be a picosecond-domain laser to deliver much higher energy with a shorter pulse duration than a Q-switched laser. In certain embodiments, the source of laser light 103 can be a long-pulsed laser with a 308 nm, 511 nm, 532 nm, 578 nm, 755 nm, or 1064 nm wavelength. In certain embodiments, the source of laser light can be an infrared laser (e.g. 1450 nm, etc.), a thulium laser (e.g. 1927 nm, etc.), or any other lasers including wavelengths, such as 1210 nm, 1728 nm, 1760 nm, 2306 nm, and 2346 nm.

To induce vasoconstriction in the dermis of treatment site 120, the temperature of cooling unit 108 can be between −30° C. and 0° C., preferably between −20° C. and 0° C. Medium 104 can be directly or indirectly (e.g. via Metal unit 109) cooled by cooling unit 108 to reach the temperature between −30° C. and 0° C., preferably between −20° C. and 0° C., as well. Contact surface 107 of medium 104 can be in contact with the surface of treatment site 120 to lower the temperature of treatment site 120. To maintain the dermal vasoconstriction, the temperature of treatment site 120 can be maintained between 0° C. and 20° C., preferably between 5° C. and 15° C., at the surface by adjusting the cooling time and the temperature of cooling unit 108. In a preferred embodiment, the temperature of treatment site 120 is also maintained between 5° C. and 15° C. at the surface.

When treatment site 120 is cooled to a temperature sufficient to induce dermal vasoconstriction, laser light 103 can be administered at 0-3000 J/cm$^2$. In certain embodiments, laser light 103 can be administered at 0.5-3000 J/cm$^2$. In certain embodiments, 0-1000 J/cm$^2$ can be administered with a long pulsed Nd:YAG laser. In certain embodiments, 0-3000 J/cm$^2$ can be administered with a yellow laser (e.g. 511 nm, 578 nm, etc.). Generally, 0-100 J/cm$^2$ can be administered with a Q-switched laser or any other laser applicable to this method. In certain embodiments, laser light 103 can be administered at 0-5 J/cm$^2$. In preferred embodiments, laser light 103 can be administered at 2-4 J/cm$^2$.

When the medium is cooled to the temperature range of between −30° C. to 0° C., fogging of the medium can occur because water from the ambient air can condensate on the surface of medium and freeze. This can lead to scattering of the laser light, which can affect the efficiency and safety of the laser treatment. In certain embodiments, fogging can be prevented by making medium 104 with two or more portions, each portion having a material with a different thermal conductivity than the other portions. For efficient cooling of treatment site 120, the portion in contact with the skin can be made of a material with the highest thermal conductivity. In certain embodiments, medium 104 can include first portion 105 and second portion 106, where second portion 106 has higher thermal conductivity than first portion 105.

In certain embodiments, first portion 105 can include quarts, sapphire, crystal, poly(methyl methacrylate), or polystyrene. In certain embodiments, second portion 106 can include quarts, sapphire, crystal, poly(methyl methacrylate), or polystyrene. In certain embodiments, the first portion can include crystal, and the second portion can include sapphire.

In certain embodiments, an antifreeze 140 can be applied between contact surface 107 and treatment site 120 to prevent fogging of contact surface 107. Antifreeze 140 should effectively transmit light even below the freezing temperature. Antifreeze 140 can be applied on contact surface 107 or on the surface of treatment site 120. In certain embodiments, antifreeze 140 can include glycerin and/or oil.

Figure 5:
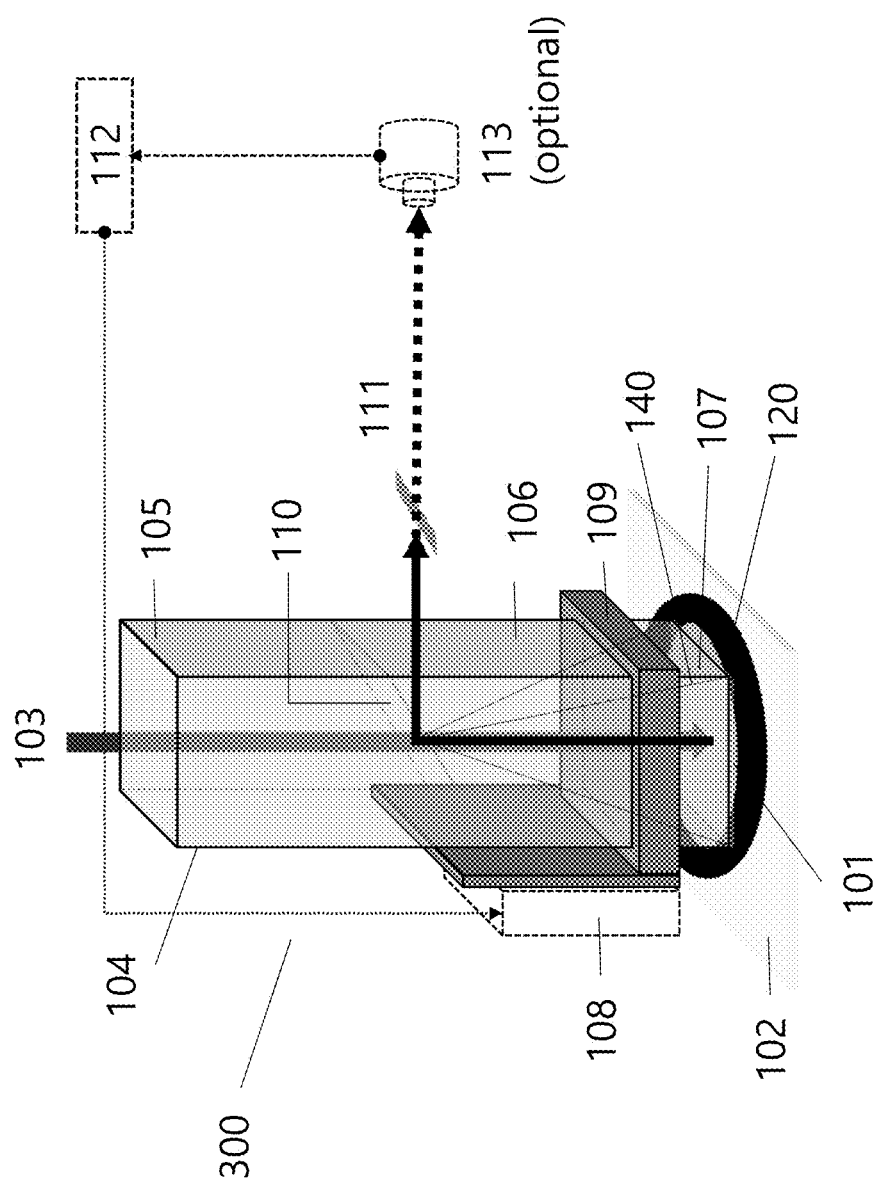

As depicted in FIG. 5, a system 300 can include device 200 as shown in FIG. 4 and a controller 112. In certain embodiments, system 300 can further include a beam splitter 110 between first portion 105 and second portion 106 to classify, pass, and/or reflect image 111 of treatment site 120. In certain embodiments, controller 112 can identify, process and analyze image 111 obtained by beam splitter 110. Beam splitter 110 can send an image including skin lesion 101 to image-capturing device 113. In certain embodiments, the image can be a real-time image. In certain embodiments, controller 112 can be operatively coupled to image-capturing device 113 to analyze characteristics of skin lesion 101 and to guide laser light 103 to treat skin lesion 101 according to the characteristics. The characteristics of the skin lesion can include location, boundary, size, thickness, and pigment level (i.e. pigment density or concentration) of the lesion. Based on these characteristics, various parameters of laser light 103, such as the beam size, frequencies, and beam-to-beam overlapping ratio, can be determined.

In certain embodiments, controller 112 can be operatively coupled to cooling unit 108 to the temperature sensor (not shown). The temperature sensor can detect temperature(s) of cooling unit 108, a temperature of medium 104, and/or a temperature of treatment site 120. In certain embodiments, controller 112 can be operatively coupled to the temperature sensor to control the temperature(s) of cooling unit 108, a temperature of medium 104, and/or a temperature of treatment site 120.

Figure 6:
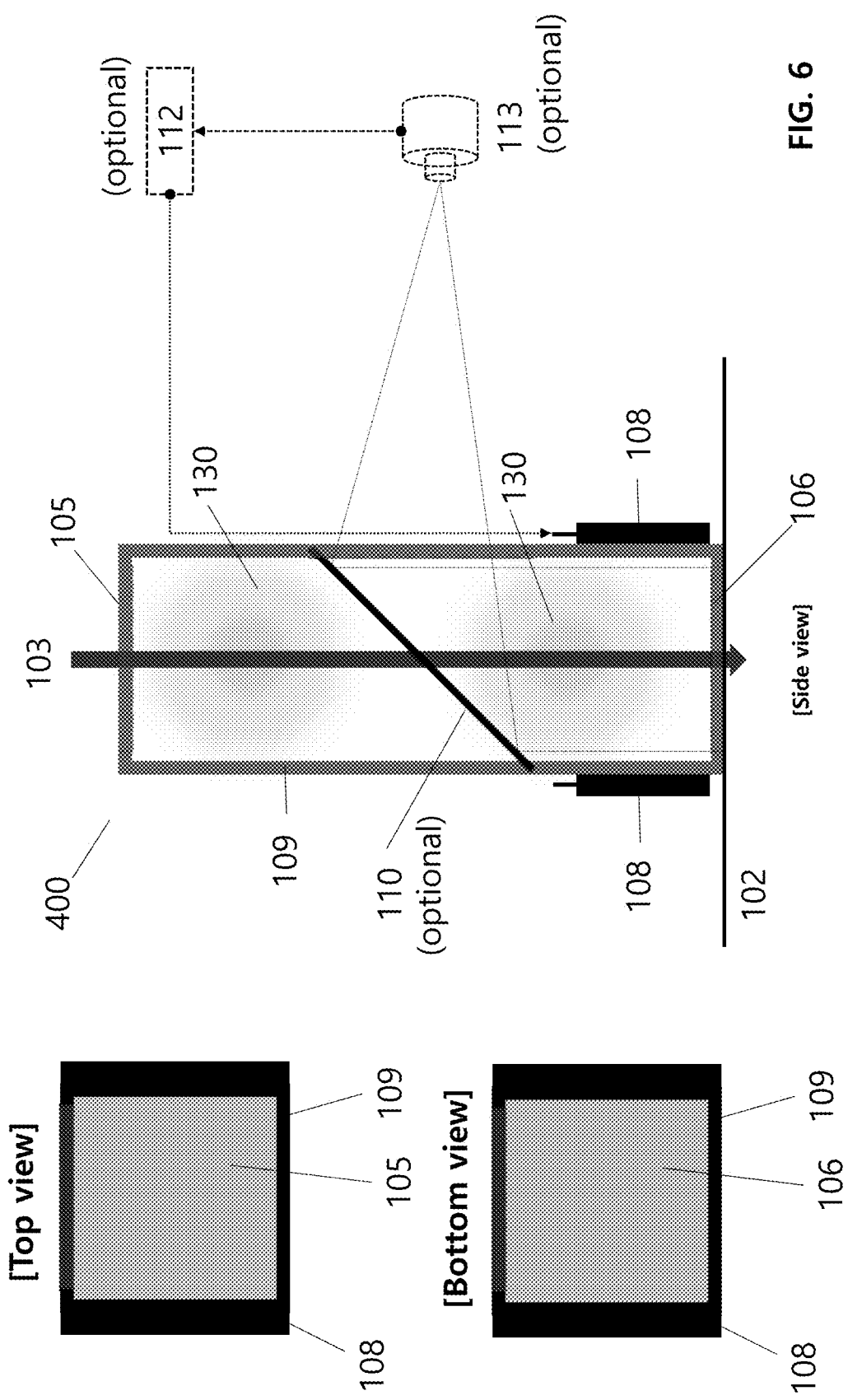
Figure 7:
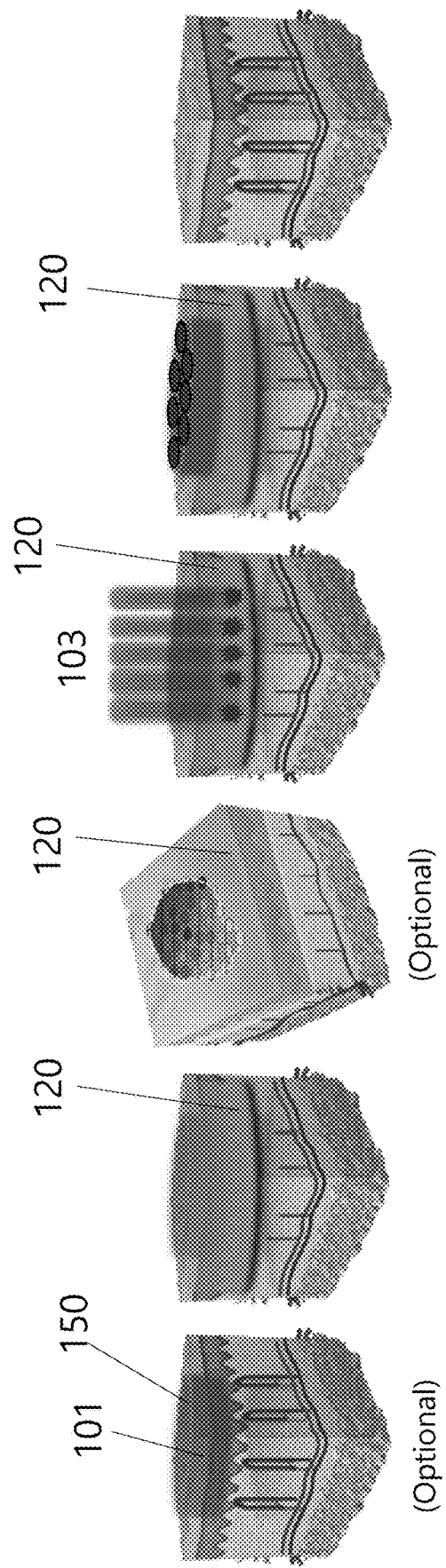
FIG. 7A shows that treatment site can be pre-treated with a local anesthetic and epinephrine to promote further vasoconstriction.
FIG. 7B shows a step of lowering the temperature of treatment site to a target temperature range sufficient to induce vasoconstriction in a dermis of treatment site.
FIG. 7C shows a step of administering laser light 103 to the skin lesion while maintaining the temperature of treatment site 120 within the target temperature range.
FIG. 7D shows that this method can minimize the damages on the dermal vasculature while treating the skin lesion.
FIG. 7E shows that side effects, such as PLE, PIH, and scars, can be significantly reduced.
FIG. 7F shows analysis using the lesion recognition algorithm including capturing and analyzing the image of skin lesion 101 for its characteristics, such as location, boundary, size, thickness, and pigment level.

As depicted in FIG. 6, device 400 can include first portion 105 and second portion 106 separated by sealed air 130. In certain embodiments, metal part 109 as well as first portion 105 and second portion 104 can constitute a sealed path for laser light 103. In certain embodiments, beam splitter 110 can be place between first portion 105 and second portion 106 to classify, pass, and/or reflect image 111 of treatment site 120. In certain embodiments, image capturing device 113, and/or controller 112 can be included.

FIGS. 7A, 7B, 7C, 7D, and 7E show the same schematics as FIGS. 2A, 2B, 2C, 2D, and 2E, respectively, for laser treatment for skin lesion 101 under dermal vasoconstriction including analysis using a lesion recognition algorithm. A method for treating skin legion 101 in skin 102 using laser light 103 while minimizing undesirable side effects of the laser can further include analysis using the lesion recognition algorithm including capturing and analyzing the image of skin lesion 101 for its characteristics, such as location, boundary, size, thickness, and pigment level (FIG. 7F).

Figure 8:
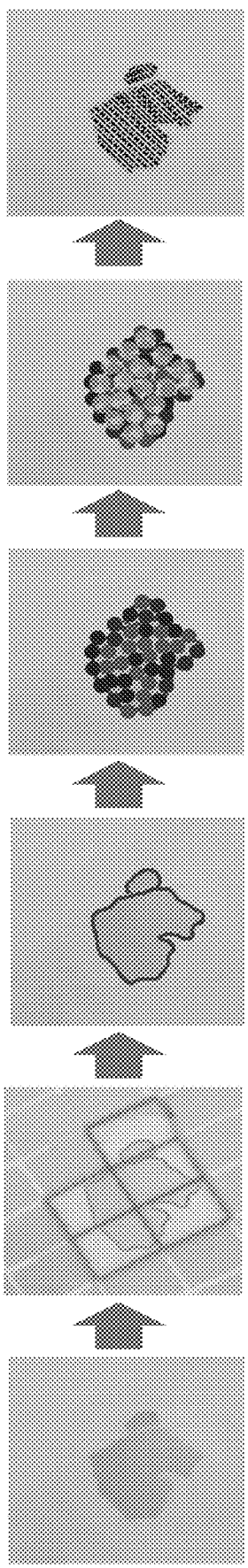
FIG. 8A shows how the lesion can be identified by controller.
FIG. 8B shows how characteristics of the lesion can be analyzed.
FIG. 8C shows how the boundary of laser irradiation can be determined.
FIG. 8D shows that based on the characteristics of the lesion, various parameters, such as the beam size, frequencies, and beam-to-beam overlapping ratio appropriate for each shot can be calculated and administered accordingly.
FIG. 8E shows that in certain embodiments, additional laser shots can be further administered to any area that has been missed or requires a certain degree of beam-to-beam overlapping.
FIG. 8F shows that in certain embodiments, any post-laser treatment can be performed after the laser treatment.

FIGS. 8A-8F show an example of the lesion recognition algorithm to treat a skin lesion. In certain embodiments, the lesion can be identified by controller 112 (FIG. 8A). The characteristics of the lesion can be analyzed, and the boundary of laser irradiation can be determined (FIGS. 8B and 8C). Based on the characteristics of the lesion, various parameters, such as the beam size, frequencies, and beam-to-beam overlapping ratio appropriate for each shot can be calculated and administered accordingly (FIG. 8D). In certain embodiments, additional laser shots can be further administered to any area that has been missed or requires a certain degree of beam-to-beam overlapping (FIG. 8E). In certain embodiments, any post-laser treatment can be performed after the laser treatment (FIG. 8F). Although these steps are described in detail, this embodiment is just an example, and those skilled in the art should understand that they can make various changes, substitutions, switch or orders, and alterations without departing from the spirit and scope disclosed herein.

Figure 9:
FIG. 9 is an illustration of laser treatment with the lesion recognition algorithm.

FIG. 9 is an illustration of laser treatment with the lesion recognition algorithm. The intensity and the coordinates of each laser shot can be precisely controlled based on the lesion recognition algorithm so that a single shot of laser light can be administered for any given location to treat the skin lesion. This can eliminate the problems of uneven irradiation, over-irradiation, or under-irradiation of laser light.

Figure 10B:
FIG. 10B shows a photo a treatment site immediately after the laser treatment according to the instant method.
Figure 10A:
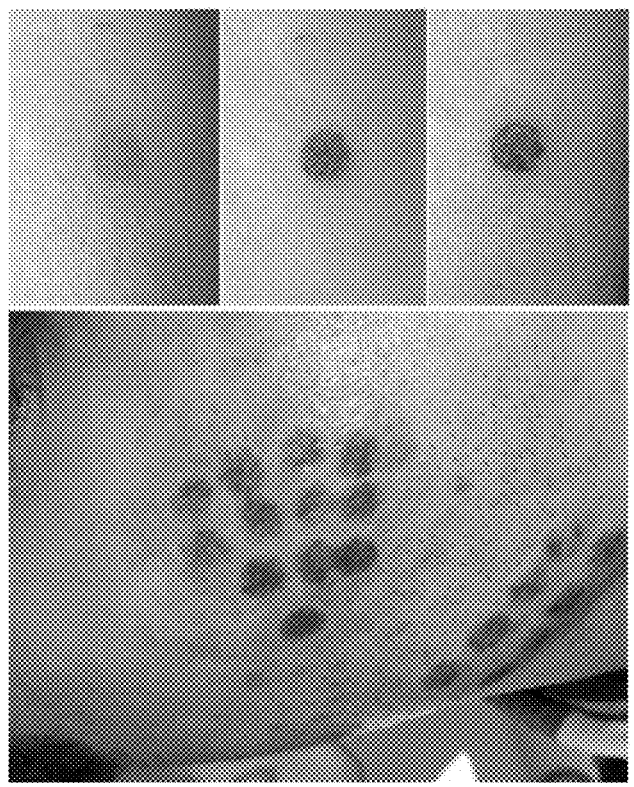
FIG. 10A shows photos of a treatment site immediately after the conventional laser treatment.
Figure 12A:
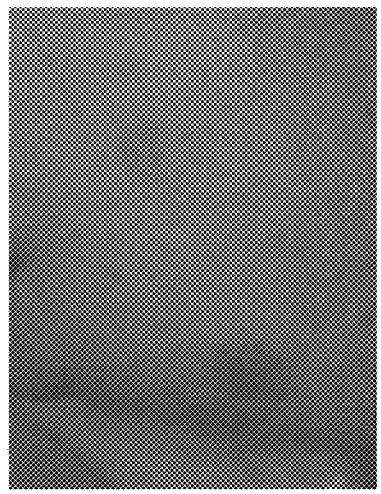
FIG. 12A shows a photo before the laser treatment according to the instant method in one patient.
Figure 12B:
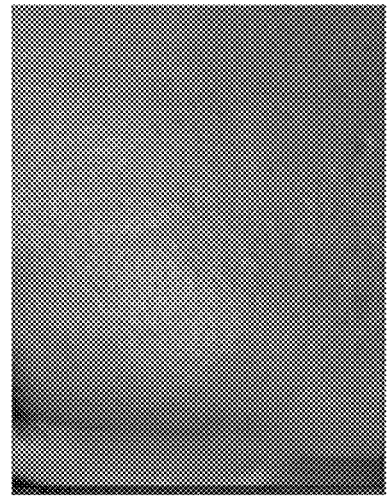
FIG. 12B shows a photo of the patient in FIG. 12A two weeks after the laser treatment according to the instant method.
Figure 12C:
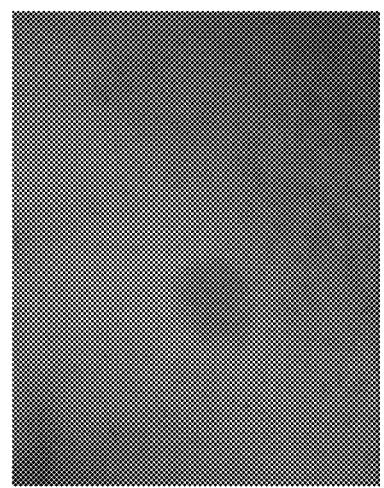
FIG. 12C shows a photo before the laser treatment according to the instant method another patient.
Figure 12D:
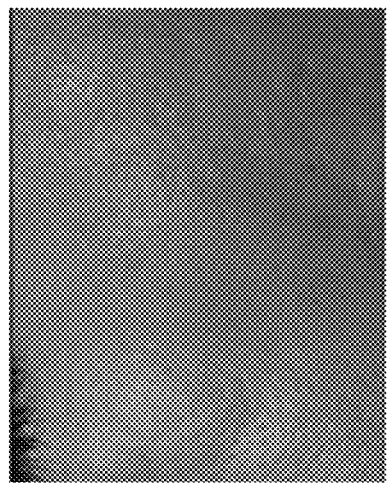
FIG. 12D shows a photo of the patient in FIG. 12C two weeks after the laser treatment according to the instant method.

The laser treatment according to the instant method can significantly reduce common side effects of the conventional laser treatment, such as pain, edema, petechiae, and ecchymoses, even with a much higher level of laser energy than the conventional laser treatment method. FIG. 10A shows photos of a pigmented lesion immediately after the conventional laser treatment with the Q-switched 532 nm laser with 0.6-1.0 J/cm$^2$ fluence of energy. The photo on the left column show the treatment area immediately after the conventional laser treatment, showing petechiae and purpuric dermal edema on the treatment site. The photos on the right column show the treatment area at 1 minute (top), 5 minutes (middle), and 30 minutes (bottom) after the conventional laser treatment, demonstrating the aggravating side effects over time. FIG. 10B shows a photo of the treatment area immediately after the laser treatment according to the instant method with the Q-switched 532 nm laser with 3 J/cm$^2$ fluence of energy. Only immediate darkening was observed without any petechiae, hemorrhage, or dermal edema.

FIG. 11A is a photo showing treatment of epidermis including the pigmented lesion after the laser treatment according to the instant method. For example, a fluence of about 2-4 J/cm$^2$ can be administered to the pigmented lesion using the Q-switched 532 nm Nd:YAG laser to treat the pigmented lesion. When this level of energy is applied to the pigmented lesion at a single pass while cooling and maintaining the surface of treatment site between 0° C. to 20° C., only epidermis of pigmented lesion is peeled off about two weeks after the treatment as shown in FIG. 11A. No damage in dermis is observed. This method can be used as a substitution for a traditional ablative laser surgery without actually ablating the tissue, thereby preventing serious side effects, such as PLE, PIH, and scars. Because major chromophores in the skin for the Q-switched 532 nm Nd:YAG laser are melanin and oxyhemoglobin, when oxyhemoglobin is largely removed from the treatment site by dermal vasoconstriction, the only remaining chromophore, melanin, which is mostly located in the basement membrane between the epidermis and dermis, can absorb most of the energy applied to the treatment site (FIG. 11B). As a result, epidermis including the pigmented lesion can be treated without damaging dermis, which enables much faster recovery compared to the traditional ablative laser surgery.

Figures 13A, 13B, 13C, 13D:
FIG. 13A shows a photo before the conventional $CO_2$ laser treatment.
FIG. 13B shows a photo of a pigmented lesion one month after the conventional $CO_2$ laser treatment.
FIG. 13C shows a photo of a pigmented lesion two months after the conventional $CO_2$ laser treatment.
FIG. 13D shows a photo of a pigmented lesion nine months after the conventional $CO_2$ laser treatment.

The laser treatment according to the instant method can result in much better long-term prognosis than the conventional laser treatment method. FIGS. 12A-12D show photos before and 2 weeks after the laser treatment according to the instant method. Photos of two patients with pigmented lesions before (FIGS. 12A and 12C) and 2 weeks after the treatment according to the instant method (FIGS. 12B and 12D) are shown. No PIH or PLE was observed in either case, and full recovery was observed for each patient only about 2 weeks after the treatment. FIGS. 13A-13D show photos of a pigmented lesion before treatment (FIG. 13A), 1 month (FIG. 13B), 2 months (FIG. 13C), and 9 months (FIG. 13D) after the conventional ablative CO$_2$ laser treatment. Significant levels of PLE and PIH were observed at least up to 2 months (FIGS. 13B and 13C), and PIH still remained 9 months after the treatment (FIG. 13D).

As non-limiting examples, the following table shows comparison of the typical fluence ranges between the conventional laser treatments and the laser treatments according to the instant method ("VSLS") for epidermal and/or dermal pigmented lesions.

| Laser Type* | Fluence for Conventional Methods | Fluence for the Instant Method ("VSLS") |
| --- | --- | --- |
| Q-switched 532 nm Nd:YAG** | 0.5-1.0 J/cm$^2$ | 3.0-6.4 J/cm$^2$ |
| Q-switched 694 nm ruby** | 7-9 J/cm$^2$ | 9-14 J/cm$^2$ |
| Long pulsed 755 nm alexandrite*** | Starting at 25 J/cm$^2$ | Starting at 40 J/cm$^2$ |

*All based on the laser spot size of 3 mm.
**Based on typical pulse durations of Q-switched lasers (e.g. 5-100 ns).
***Based on 0.3 ms pulse duration.

Figure 14:
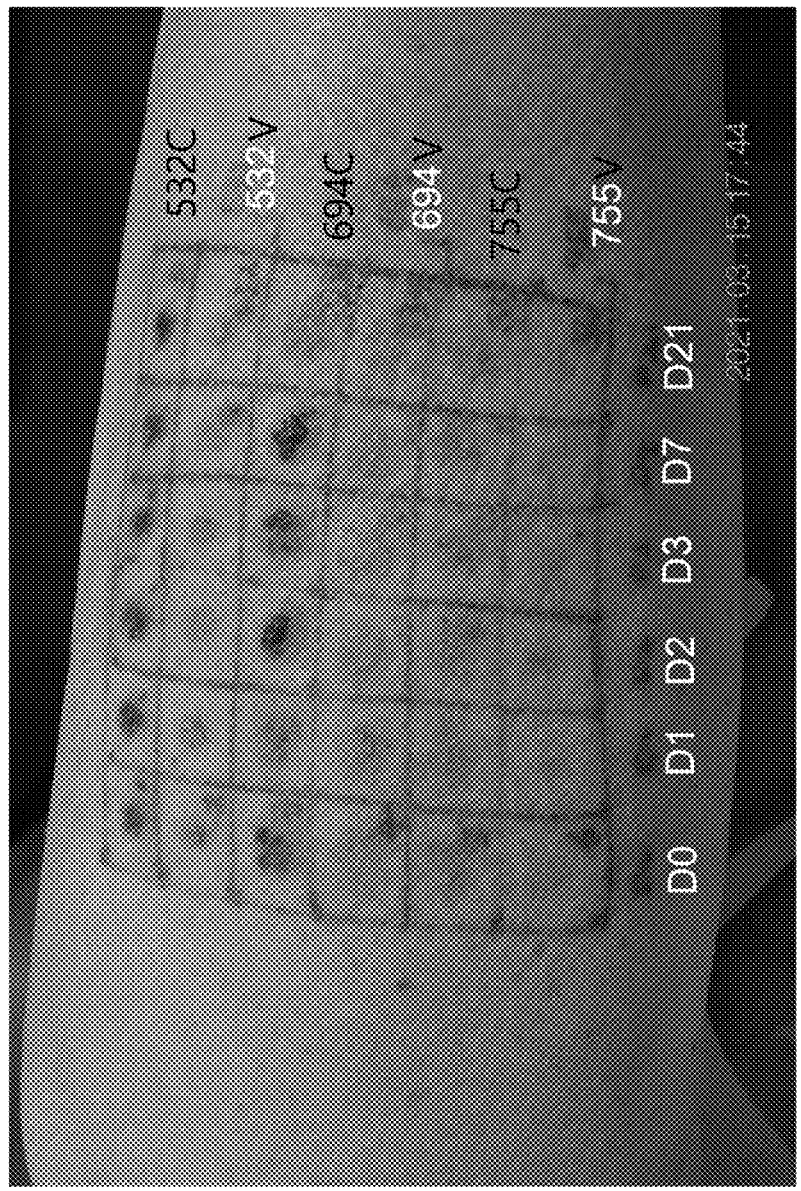
FIG. 14 shows comparison between the conventional laser treatment and the laser treatment according to the instant method.

FIG. 14 shows the exemplary comparison between the conventional method and the instant method for Q-switched 532 nm Nd:YAG (Qx-max, 3 mm laser spot size, Fotona Inc., Slovenia), Q-switched 694 nm ruby (Sinon-I, 3 mm laser spot size, Alma Inc., Germany), and long pulsed 755 nm alexandrite (Pento 755 nm, 3 mm laser spot size, NSON, South Korea) lasers, respectively. The rows marked as 532C, 694C, and 755C represent control treatment spots according to the conventional method with 532 nm, 694 nm, and 755 nm lasers, respectively. The rows marked as 532V, 694V, and 755V represent treatment spots according the instant method with 532 nm, 694 nm, and 755 nm lasers, respectively. Column D0 (day 0) shows the treatment spots that were biopsied for histological examination immediately after each treatment. Columns D1, D2, D3, and D7 show the treatment spots that were biopsied 1 day, 2 days, 3 days, and 7 days after the respective treatment. D21 spots (21 days after the treatment) were not biopsied.

Figure 15:
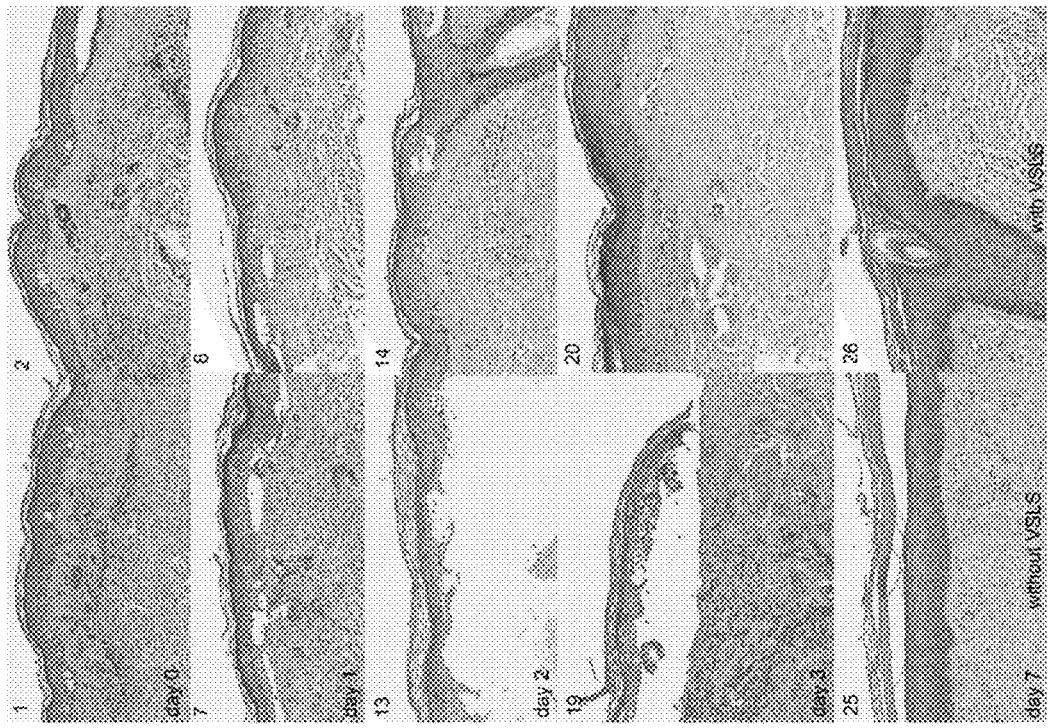
FIG. 15 shows histological comparison between the conventional laser treatment and the laser treatment according to the instant method for the Q-switched 532 nm Nd:YAG laser.

For the Q-switched 532 nm Nd:YAG laser with 3 J/cm$^2$, on day 0 and day 1, both conventional method and the instant method resulted in epidermal and dermal vasculature damages. On day 2, the conventional treatment method resulted in separation of epidermis and dermis with significant damages in dermis. In contrast, the instant method did not cause damages in dermal vasculature and both epidermis and dermis recovered very quickly. FIG. 15 shows the histological comparison of the treatment spots for the Q-switched 532 nm Nd:YAG laser for the conventional method (left column) and the instant method (right column).

Figure 16:
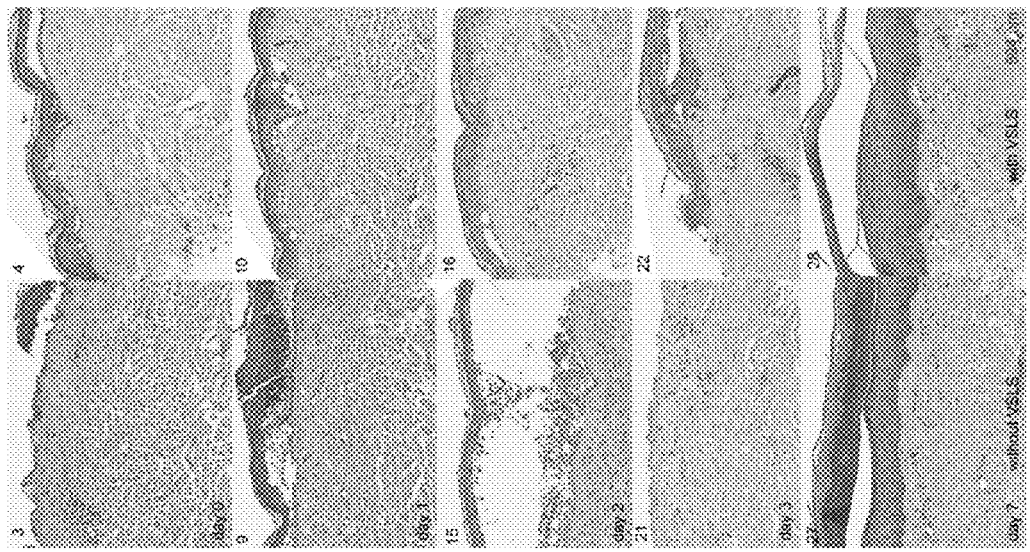
FIG. 16 shows histological comparison between the conventional laser treatment and the laser treatment according to the instant method for the Q-switched 694 nm ruby laser.

For the Q-switched 694 nm ruby laser with 9 J/cm$^2$, the results were similar to those of the 532 nm Nd:YAG laser. FIG. 16 shows the histological comparison of the treatment spots for the Q-switched 694 nm ruby laser for the conventional method (left column) and the instant method (right column).

Figure 17:
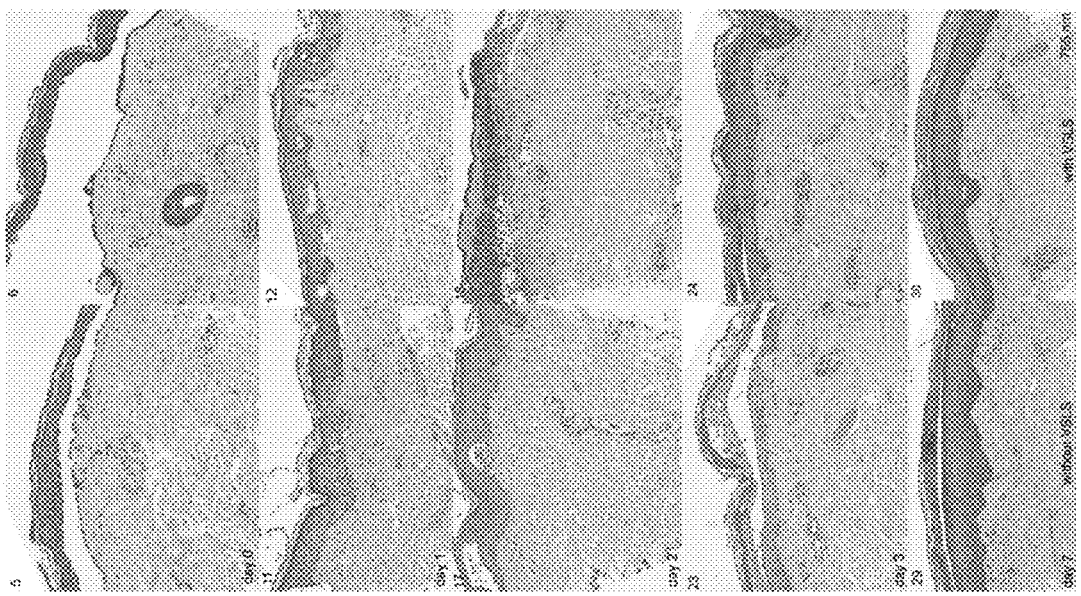
FIG. 17 shows histological comparison between the conventional laser treatment and the laser treatment according to the instant method for the long pulsed 755 nm alexandrite laser.

For the long pulsed 755 nm alexandrite laser with 40 J/cm$^2$, the recovery of the dermis was much faster from day 3 when the instant method was used compared to the conventional method. FIG. 17 shows the histological comparison of the treatment spots for the long pulsed 755 nm laser for the conventional method (left column) and the instant method (right column).

The methods and devices disclosed herein can be used to treat various pigmented skin lesions including seborrheic keratosis, melasma, freckles, solar lentigo, melanocytic nevus, and dermal melanocytosis. These methods and devices can also be used to treat nevus of Ota, congenital melanocytic nevus, Becker's nevus, tattoo removal, laser epilation, sebaceous glands, and other vascular, pigmentary skin lesions and benign skin tumors by varying wavelengths, pulse widths, and other parameters and types of laser. These methods and devices can also be used to treat any other skin lesions including non-cancerous, precancerous lesions and non-melanoma skin cancers originated from epidermis, including viral warts, actinic keratosis, actinic chelitis, Bowen's disease, Bowenoid papulosis, superficial basal cell carcinoma, squamous cell carcinoma in situ, minimally invasive squamous cell carcinoma and extramammary Paget's disease.

Other embodiments are within the scope of the following claims.

What is claimed is:

1. A method for treating a skin lesion comprising:
   lowering a temperature of a treatment site comprising the skin lesion to a temperature range sufficient to induce vasoconstriction in a dermis of the treatment site; and
   administering a laser light through a medium to the skin lesion while maintaining the temperature of the treatment site within the temperature range,
   wherein the medium includes a first portion and a second portion, wherein the laser light is transmitted through the first portion and the second portion sequentially, the second portion includes a contact surface for contacting the treatment site; wherein the second portion has a higher thermal conductivity than the first portion,
   and wherein the first portion is in contact with the second portion.

2. The method of claim 1, wherein the first portion and the second portion are optically transparent.

3. The method of claim 1, wherein the lowering the temperature of the treatment site includes contacting the treatment site with the contact surface of the second portion of the medium.

4. The method of claim 3, wherein the contacting the treatment site with the contact surface of the second portion of the medium includes compressing the surface of the treatment site with the contact surface of the second portion of the medium.

5. The method of claim 1, wherein the lowering the temperature of the treatment site includes administering a drug to induce vasoconstriction of the treatment site before administering the laser light.

6. The method of claim 1, wherein the laser light has a wavelength between about 300 nm and about 2500 nm.

7. The method of claim 1, wherein the laser light has a fluence of 0-3000 J/cm$^2$.

8. The method of claim 1, wherein the temperature range is between 0° C. and 20° C.

9. A device for treating a skin lesion comprising:
   a source for generating a laser light;
   a medium for transmitting the laser light,
       wherein the medium includes a first portion and a second portion,
       wherein the laser light is transmitted through the first portion and the second portion sequentially,
       wherein the second portion includes a contact surface for contacting a treatment site comprising the skin lesion;
       wherein the second portion has a higher thermal conductivity than the first portion,
       and wherein the first portion is in contact with the second portion.

10. The device of claim 9, wherein the laser light has a wavelength between about 300 nm and about 2500 nm.

11. The device of claim 9, wherein the laser light has a fluence of 0-3000 J/cm$^2$.

12. The device of claim 9, wherein the first portion and the second portion are optically transparent.

13. The device of claim 9, wherein the first portion includes quarts, sapphire, crystal, poly(methyl methacrylate), or polystyrene.

14. The device of claim 9, further comprising a cooling unit to lower a temperature of the medium to a target temperature range.

15. The device of claim 14, wherein the target temperature range of the medium is from −30° C. to 0° C.

16. A system for treating a skin lesion comprising:
    a source for generating a laser light;
    a medium for transmitting the laser light, wherein the medium includes a first portion and a second portion, wherein the laser light is transmitted through the first portion and the second portion sequentially, the second portion includes a contact surface for contacting a treatment site comprising the skin lesion; wherein the second portion has a higher thermal conductivity than the first portion, and wherein the first portion is in contact with the second portion;
    a cooling unit to lower a temperature of the medium to a target temperature range; and
    a controller operatively coupled to the image-capturing device to analyze one or more characteristics of the skin lesion, wherein the controller guides the laser light to treat the skin lesion according to the one or more characteristics.

17. The system of claim 16, wherein the laser light has a wavelength between about 300 nm and about 2500 nm.

18. The system of claim 16, wherein the laser light has a fluence of 0-3000 J/cm$^2$.

19. The system of claim 16, wherein the first portion and the second portion are optically transparent.

20. The system of claim 16, wherein the target temperature range of the medium is from −30° C. to 0° C.

21. A system for treating a skin lesion comprising:
- a source for generating a laser light;
- a medium for transmitting the laser light, wherein the medium includes a first portion and a second portion, wherein the laser light is transmitted through the first portion and the second portion sequentially, the second portion includes a contact surface for contacting a treatment site comprising the skin lesion;
    - wherein the second portion has a higher thermal conductivity than the first portion, and
    - wherein the first portion is in contact with the second portion; and
- a cooling unit to lower a temperature of the medium to a target temperature range.

22. The system of claim 21, wherein the laser light has a wavelength between about 300 nm and about 2500 nm.

23. The system of claim 21, wherein the laser light is a pulsed light.

24. The system of claim 21 wherein the laser light has a fluence of 0-3000 J/cm$^2$.

25. The system of claim 21, wherein the first portion and the second portion are optically transparent.

26. The system of claim 21, wherein the target temperature range of the medium is from −30° C. to 0° C.

* * * * *